(12) United States Patent
Smith et al.

(10) Patent No.: US 7,066,174 B1
(45) Date of Patent: Jun. 27, 2006

(54) BREATHING ASSISTANCE APPARATUS

(75) Inventors: Nicholas Charles Alan Smith, Auckland (NZ); Alastair Edwin McAuley, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 492 days.

(21) Appl. No.: 09/662,203

(22) Filed: Sep. 14, 2000

(30) Foreign Application Priority Data

Sep. 23, 1999 (NZ) ................................................ 337993

(51) Int. Cl.
*A62B 9/02* (2006.01)

(52) U.S. Cl. ............................ 128/205.24; 128/204.18; 128/207.14; 128/207.18

(58) Field of Classification Search ............ 128/200.14, 128/200.29, 201.13, 201.25, 201.27, 201.28, 128/203.2, 203.16, 203.17, 203.26, 204.14, 128/204.17, 204.18, 204.21, 204.26, 205.11, 128/205.13–205.18, 205.24, 207.14–207.18
See application file for complete search history.

(56) References Cited

U.S. PATENT DOCUMENTS

| | | | | |
|---|---|---|---|---|
| 4,088,131 A | * | 5/1978 | Elam et al. ............ | 128/205.13 |
| 4,224,939 A | * | 9/1980 | Lang ..................... | 128/205.13 |
| 4,655,213 A | | 4/1987 | Rapoport et al. | |
| 5,065,756 A | | 11/1991 | Rapoport | |
| 5,163,424 A | * | 11/1992 | Kohnke ................. | 128/205.13 |
| 5,398,673 A | * | 3/1995 | Lambert ................ | 128/202.28 |
| 5,538,002 A | * | 7/1996 | Boussignac et al. ... | 128/207.16 |
| 5,584,288 A | * | 12/1996 | Baldwin ................ | 128/202.28 |
| 5,657,752 A | | 8/1997 | Landis et al. | |
| 5,803,065 A | | 9/1998 | Zdrojkowski et al. | |

FOREIGN PATENT DOCUMENTS

GB        1238649        7/1971

* cited by examiner

*Primary Examiner*—Glenn K. Dawson
(74) *Attorney, Agent, or Firm*—Trexler, Bushnell, Giangiorgi, Blackstone & Marr, Ltd.

(57) ABSTRACT

A valve for use in a CPAP system or any stem at a pressure above ambient which vents the pressurised gases from the blower during expiration. Due to the pressure-flow characteristics of the blower this results in the patient having a much lower airway pressure during expiration making breathing easier. The valve includes a movable member which blocks flow from the blower to the patient during exhalation and vents externally. During inhalation gases flow normally from the blower to the patient.

18 Claims, 4 Drawing Sheets

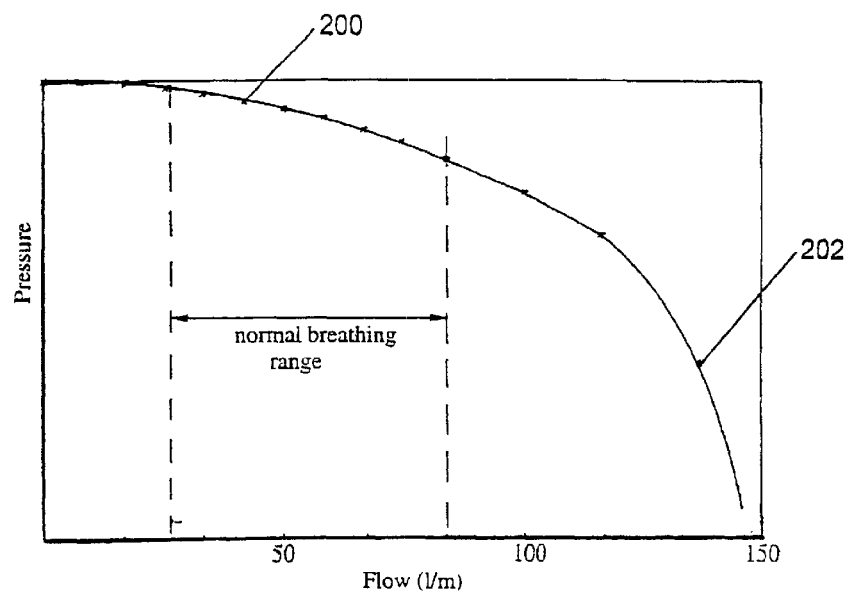
FIG. 4
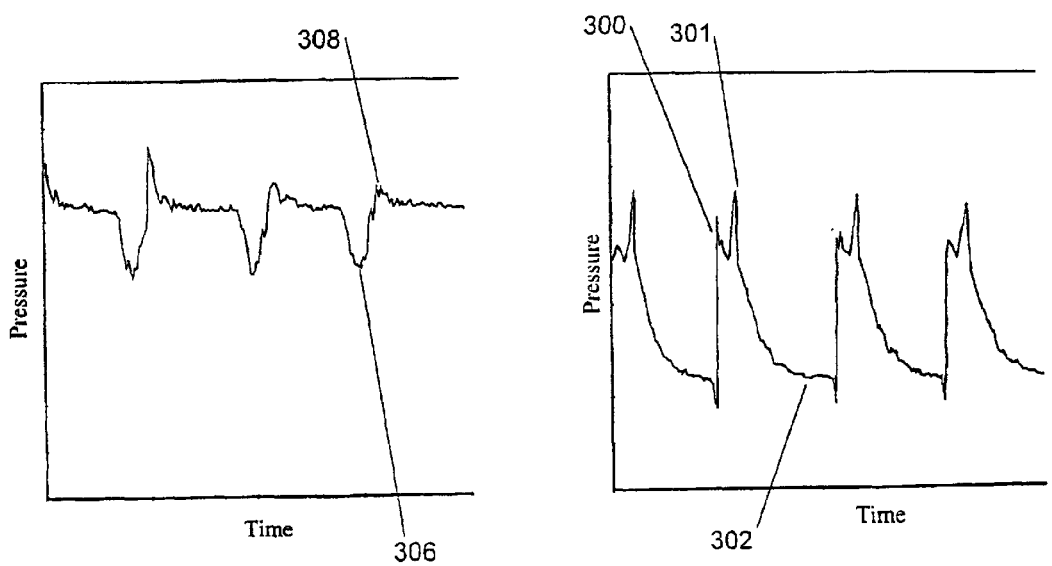
FIG. 6               FIG. 7

BREATHING ASSISTANCE APPARATUS

BACKGROUND TO THE INVENTION i) Field of the Invention

This invention relates to valves particularly though not solely for inclusion in the breathing circuit of a respirator.

ii) Summary of the Prior Art

A medical breathing circuit such as might be used in a Continuous Positive Airway Pressure Respirator (CPAP) includes an inspiratory gases tube which has one end thereof connected to the patient through an interface. For example through an endotracheal breathing tube extending into the trachea and ending just above the lungs. The other end thereof is connected to a respirator providing pressurised gases. The connection to the respirator may be direct or a self contained humidifier may be interposed.

One disadvantage of CPAP treatment is that it effectively reverses the normal breathing function. The patient has to relax to breath in and requires effort to breath out. Since normal breathing requires the exact opposite, the use of CPAP is sometimes difficult initially.

A number of devices exist to reduce the effort required by the patient to exhale. For example U.S. Pat. No. 5,657,752 assigned to Airways Associates describes a variable orifice venting aperture member in the nasal mask to help vent the exhalations. U.S. Pat. No. 5,065,756 assigned to New York University includes vent holes in the face mask for rapid discharge of exhaled air. U.S. Pat. 4,655,213 assigned to New York University includes a threshold valve to release air from the mask. Alternatively electronic methods exist such as that described in U.S. Pat. 5,803,065 assigned to Respironics have been used to improve the effectiveness of CPAP therapy.

However to some degree these existing devices are still somewhat ineffective. Also in some cases these apparatus include a bulky face mask and strapping which may be uncomfortable for the user.

SUMMARY OF THE INVENTION

It is an object of the present invention to provide a valve for a respiratory breathing circuit which will obviate the above disadvantage or will at least provide healthcare providers with a useful choice.

Accordingly in a first aspect the invention consists in a device for controlling the gas flow between a pressurised gases supply and a user, comprising:

a body portion including a first opening adapted to be in fluid communication with a pressurised gases supply, a second opening adapted to be in fluid communication with a user a first auxiliary outlet in said body portion, and valve means adapted such that during a user's inhalation, the flow of gases from said first opening is directed to said second opening, and during a user's exhalation, the flow of gases from said first opening is directed to said first auxiliary outlet.

In a second aspect the present invention consists in a system for supplying gases to a user at a pressure above ambient including a pressurised gases supply; gases delivery means for supplying said gases to said user in fluid communication with said pressurised gases supply and said user; and flow control means disposed within said gases delivery means or in fluid communication therewith, said flow control means comprising:

a body portion including a first opening adapted to be in fluid communication with said pressurised gases supply, a second opening adapted to be in fluid communication with said user a first auxiliary outlet in said body portion, and valve means adapted such that during said user's inhalation, the flow of gases from said first opening is directed to said second opening, and during said user's exhalation, the flow of gases from said first opening is directed to said first auxiliary outlet.

To those skilled in the art to which the invention relates, many changes in construction and widely differing embodiments and applications of the invention will suggest themselves without departing from the scope of the invention as defined in the appended claims. The disclosures and the descriptions herein are purely illustrative and are not intended to be in any sense limiting.

BRIEF DESCRIPTION OF THE DRAWINGS

FIG. 4 is a graph of a typical pressure/flow rate characteristics of a respirator, FIG. 6 is a graph illustrating the typical pressure profile experienced by a patient according to traditional CPAP methods, and FIG. 7 is a graph illustrating the typical pressure profile experienced by a patient according to the preferred embodiment of the present invention.

DETAILED DESCRIPTION

The present invention attempts to provide a simple to manufacture device which attempts to improve comfort levels for a user undergoing CPAP therapy. This is done by providing a four-way valve in the conduit between the respirator and the patient which allows both gases to flow to the patient and exhalations to be expelled to flow through the same conduit. This makes exhaling easier for the user, without the need for additional apparatus to be worn by the user. If the gases supplied to the user are to be humidified, the valve is positioned between the respirator and the humidifier, i.e. upstream of the humidifier.

Figure 1A:
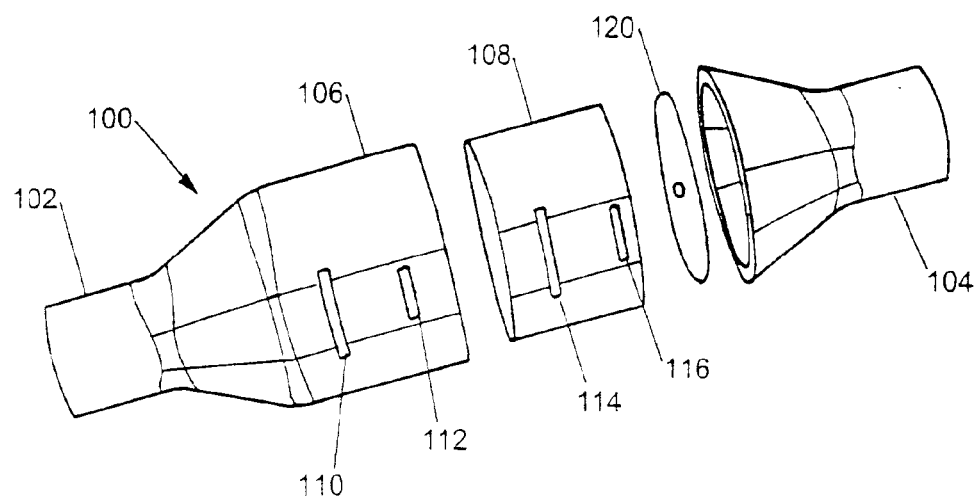
FIG. 1A is a blown out perspective view of the present invention, showing the components that fit together to form the valve.
Figure 1B:
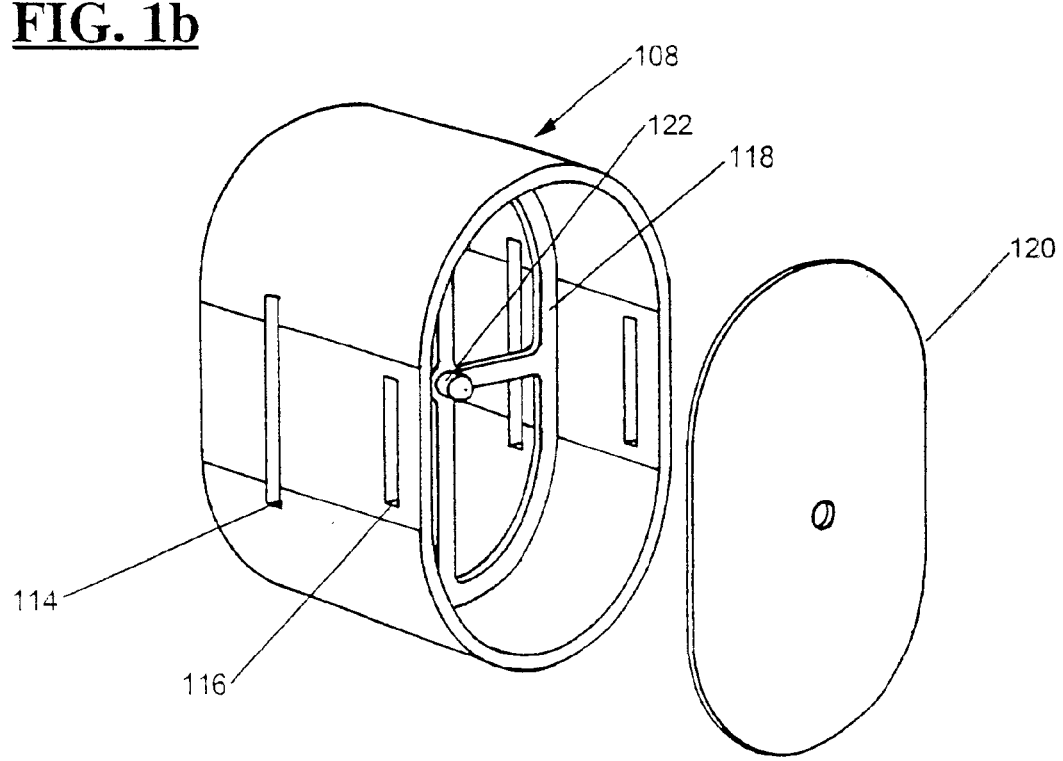
FIG. 1B is a blown out perspective view of the movable valve member according to the preferred embodiment of the present invention.

Referring now to FIGS. 1*a*, 1*b* we see the valve in more detail. The valve body 100 has two ends 102, 104 adapted for connection to a typical respiratory conduit and an enlarged centre section 106 which houses the axially moveable valve member 108. The centre section 106 includes two apertures 110 and 112 on its periphery, located either side of an imaginary central point.

The valve member 108 is of a generally hollow cylindrical construction and includes two matching apertures 114, 116 on its periphery again located either side of an imaginary centre point. Also part of the valve member 108 is a partition 118 which joined to the inner periphery of the valve member in between the two apertures 114, 116. Attached in the centre 122 of the partition 118 is a one-way valve 120 which only allows inhalatory gases to pass and at least partially blocks exhalatory gases.

In the preferred embodiment of the present invention the one way valve 120 is a sealing rubber flap attached to the partition on the patient side. This allows gas to pass from respirator to user (inhalation), but only on a minimal level from user to respirator (exhalation) in FIGS. 2 and 3. This is because the flap is designed to be not quite large enough to entirely seal around the aperture. Thus a small amount of exhalatory gases may pass.

Figure 2:
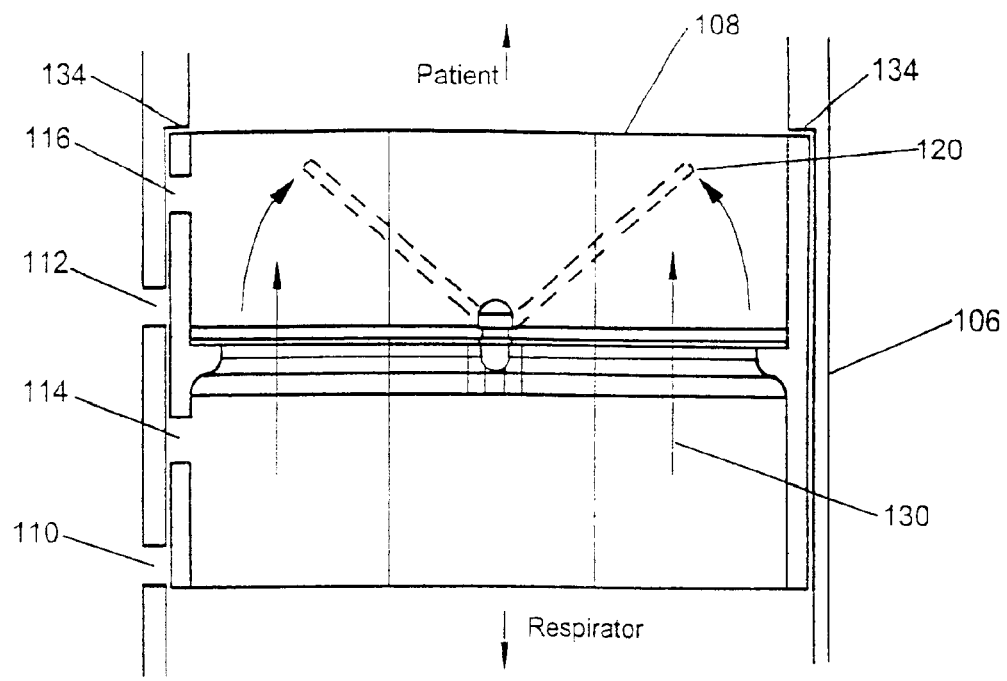
FIG. 2 is a cutaway view of the present invention during inhalation.
Figure 3:
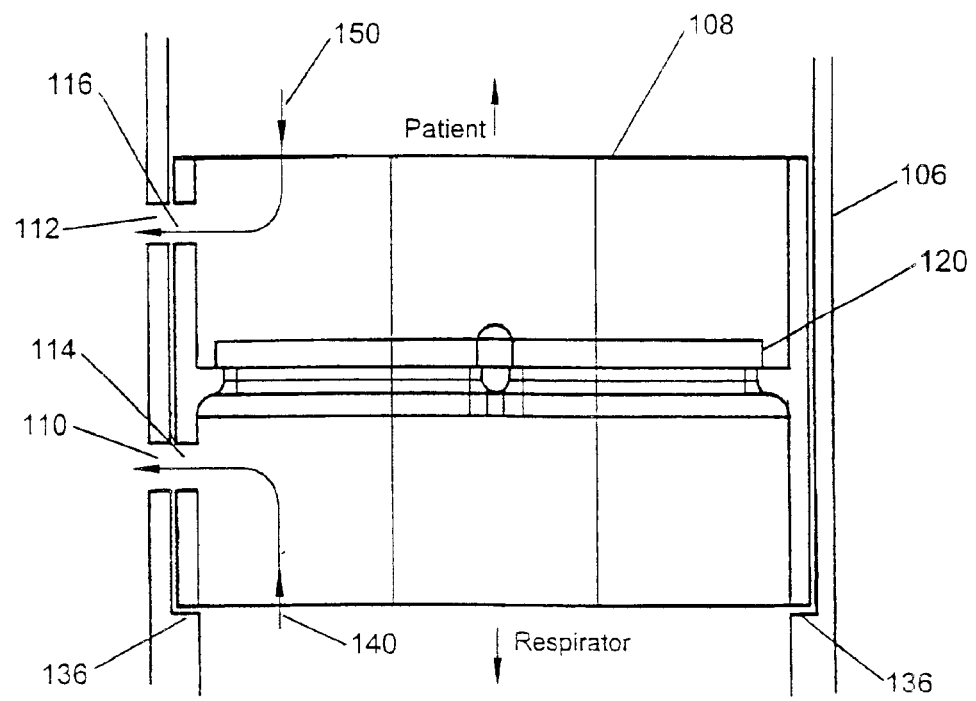
FIG. 3 is a cutaway view of the present invention during exhalation.

Referring now to FIGS. 2 and 3, the operation of the valve is now explained.

During a patient inhalation the valve member is in the open position as shown in FIG. 2. The gas flow is as designated by arrow 130, which forces the movable member 108 towards the patient, until it hits the inspiratory stops 134. The apertures in the body portion 110, 112 in this position are closed off and do not match up with the apertures in the valve member 114, 116. In this case the one-way valve is effectively in open position and provides low resistance through the valve from the respirator to the patient.

When the patient exhales, shown in FIG. 3, back pressure results on the patient side of the valve due to the one-way valve 120. This pressure forces the valve member 108 to move towards the respirator, until it hits the expiratory stops 136. Once forced to the "closed" position, the apertures 110, 112 in the body portion and the apertures in the valve member 114, 116 align. This means that gases from the respirator are discharged into the atmosphere, shown by arrow 140 and the exhalatory gases from the patient, shown by arrow 150, are also discharged into the atmosphere. This means that the back pressure that the patient experiences while exhaling is much reduced due to the typical pressure flow rate characteristics of the respirator shown in FIG. 4. During inhalation the respirator might operate at point 200. Whereas during exhalation, due to the high flow rate through aperture 110 into the atmosphere, operation might be at point 202 with correspondingly low pressure seen by the patient.

It will be appreciated that the aperture in the valve used to vent the patient's exhalations is only one possible embodiment of the present invention. It would be equally viable to have, for example, a pressure release valve in the circuit near the patient. The advantage of the present invention however is the reduced pressure delivered by the respirator, during exhalation.

Each of the valve body portion 102 and valve member 108 may be simply manufactured by injection moulding, for example a polycarbonate plastics material or other suitable plastics material.

Figure 5:
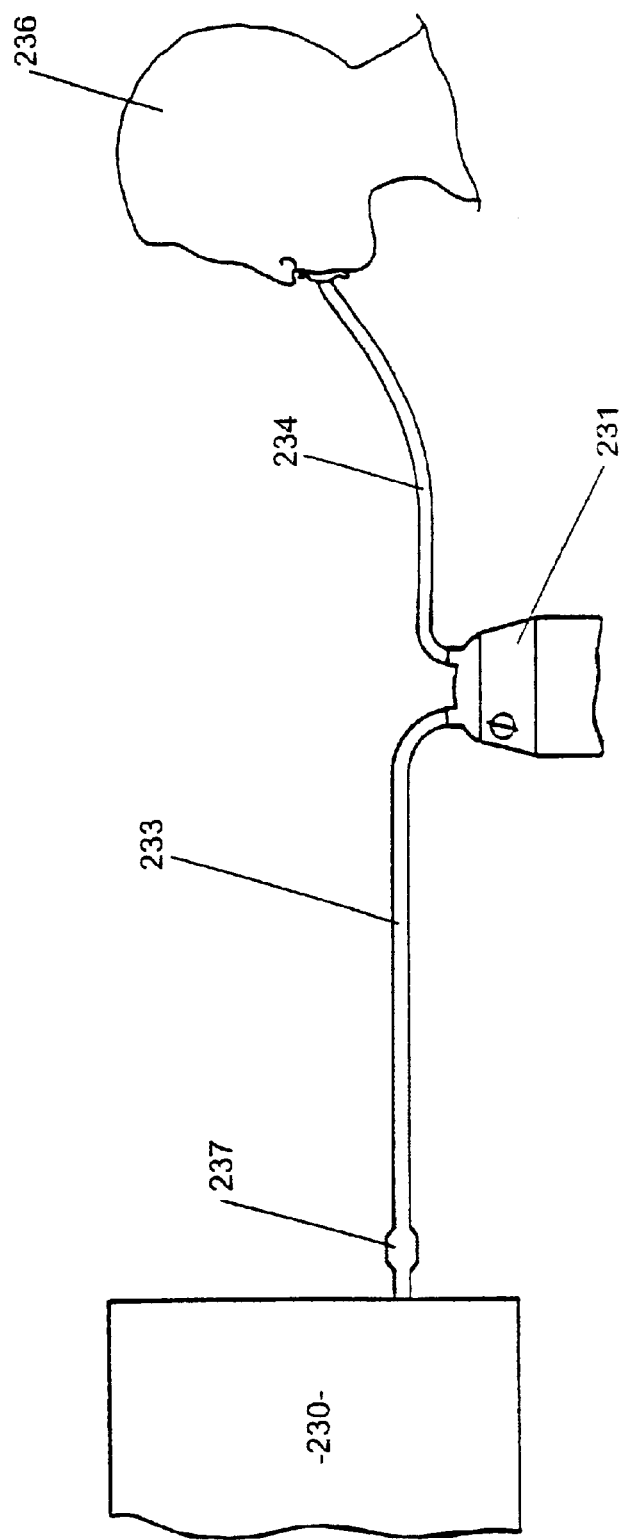
FIG. 5 is a block diagram of a typical breathing assistance apparatus circuit, according to the preferred embodiment of the present invention.

A typical respiratory humidification circuit such as might employ the present invention is shown diagrammatically in FIG. 5, and includes the respirator 230, humidifier 231, and the associated respiratory breathing tubes 233 and 234. A patient 236 under treatment is shown connected to the system. As indicated in FIG. 5 the valve of the present invention is connected between the humidifier 231 and the outlet port of the respirator 230 and is indicated by reference numeral 237.

A typical pressure profile as might be experienced by a patient treated using the present invention is shown in FIG. 7. This illustrates the high pressure during inhalation 300, the point at which the valve vents the respirator output 301, and the relatively low pressure during exhalation 302. This compares with a typical pressure profile of a patient treated without the present invention shown in FIG. 6. This illustrates that the pressure experienced during exhalation 308 is similar to that during inhalation 306.

It will be appreciated from the above description that during exhalation the patient does not have to exert as much force to exhale as would normally be the case with traditional cpap therapy. Thus the present invention provides a simple method of improving the quality of CPAP therapy without increasing the bulk of the apparatus worn by the patient.

What is claimed is:

1. A device for controlling the gas flow between a pressurised gases supply and a user, comprising:
    a body portion including a first opening adapted to be in fluid communication with a pressurised gases supply, a second opening adapted to be in fluid communication with a user,
    a first auxiliary outlet in said body portion, a second auxiliary outlet in said body portion, which during inhalation of a user is closed, and during exhalation of a user is open and in fluid communication with said second opening, said first auxiliary outlet is of an cross sectional area greater than that of said second auxiliary outlet, and
    valve means adapted such that during a user's inhalation, the flow of gases from said first opening is directed to said second opening, and during a user's exhalation, the flow of gases from said first opening is directed to said first auxiliary outlet.

2. A device as claimed in claim 1 wherein said valve means comprises an axially moveable member including means for substantially sealing inside said body portion, said member in use axially moveable within said body portion.

3. A device for controlling the gas flow between a pressurised gases supply and a user, comprising:
    a body portion including a first opening adapted to be in fluid communication with a pressurised gases supply, a second opening adapted to be in fluid communication with a user,
    a first auxiliary outlet in said body portion,
    a second auxiliary outlet in said body portion, which during inhalation of a user is closed, and during exhalation of a user is open and in fluid communication with said second opening, and
    valve means adapted such that during a user's inhalation, the flow of gases from said first opening is directed to said second opening, and during a user's exhalation, the flow of gases from said first opening is directed to said first auxiliary outlet, said valve means comprising an axially moveable member including means for substantially sealing inside said body portion, said member in use axially moveable within said body portion, said movable member including at least two apertures and said first auxiliary outlet and said second auxiliary outlet comprise apertures in said body portion which align with said apertures in said moveable member during exhalation of a user, and are closed off by solid sections of said moveable member during inhalation of a user.

4. A device as claimed in claim 3 wherein said moveable member includes a partition disposed between said apertures in said moveable member, and a one way valve allowing flow only in the direction from said first opening to said second opening.

5. A device as claimed in claims 3 or 4 wherein said first auxiliary outlet is of an cross sectional area greater than that of said second auxiliary outlet.

6. A device as claimed in claim 3 wherein said body portion including stopping means restricting the axial movement of said movable member such that during inhalation said moveable member moves towards said second opening until stopped by said stopping means whereby said apertures in said body portion are closed off by said solid sections, and during exhalation said moveable member moves toward said first opening until stopped by said stopping means whereby said apertures in said moveable member align with said apertures in said body portion.

7. A system for supplying gases to a user at a pressure above ambient comprising:
  a pressurised gases supply for supplying a continuous positive pressure above ambient,
  gases delivery means for supplying said gases to a user, said gases delivery means being in fluid communication with said pressurised gases supply, and
  flow control means disposed within said gases delivery means or in fluid communication therewith, said flow control means comprising a device for controlling the gas flow within said gases delivery means, said device including a body portion including a first opening adapted to be in fluid communication with said pressurised gases supply, a second opening for providing fluid flow to and/or from said flow control means, a first auxiliary outlet in said body portion, a second auxiliary outlet in said body portion, which during inhalation of a user is closed, and during exhalation of a user is open and in fluid communication with said second opening, and valve means adapted such that during a user's inhalation, the flow of gases from said first opening is directed to said second opening, and during a user's exhalation, the flow of gases from said first opening is directed to said first auxiliary outlet, said valve means comprising an axially movable member including at least two apertures and said first auxiliary outlet and said second auxiliary outlet comprise apertures in said body portion which align with said two apertures in said moveable member during exhalation of a user, and are closed off by solid sections of said moveable member during inhalation of a user.

8. A system as claimed in claim 7 further comprising humidification means, for humidifying said gases before delivery to said user, disposed within or in fluid communication with said gases delivery means.

9. A system as claimed in claim 7 further comprising humidification means, for humidifying said gases before delivery to said user, disposed within or in fluid communication with said gases delivery means.

10. A system as claimed in claim 7 wherein said axially moveable member includes means for substantially sealing inside said body portion, said member in use axially moveable within said body portion.

11. A system as claimed in claim 10 further comprising humidification means, for humidifyng said gases before delivery to said user, disposed within or in fluid communication with said gases delivery means.

12. A system as claimed in claim 7 further comprising humidification means, for humidifying said gases before delivery to said user, disposed within or in fluid communication with said gases delivery means.

13. A system as claimed in claim 7 wherein said moveable member includes a partition disposed between said apertures in said moveable member, and a one way valve allowing flow only in the direction from said first opening to said second opening.

14. A system as claimed in claim 13 further comprising humidification means, for humidifying said gases before delivery to said user, disposed within or in fluid communication with said gases delivery means.

15. A system as claimed in claims 10 or 13 wherein said first auxiliary outlet is of an cross sectional area greater than that of said second auxiliary outlet.

16. A system as claimed in claim 15 further comprising humidification means, for humidifying said gases before delivery to said user, disposed within or in fluid communication with said gases delivery means.

17. A system as claimed in claim 7 wherein said body portion includes stopping means restricting the axial movement of said movable member such that during inhalation said moveable member moves towards said second opening until stopped by said stopping means whereby said apertures in said body portion are closed off by said solid sections, and during exhalation said moveable member moves toward said first opening until stopped by said stopping means whereby said apertures in said moveable member align with said aperatures in said body portion.

18. A system as claimed in claim 17 further comprising humidification means, for humidifying said gases before delivery to said user, disposed within or in fluid communication with said gases delivery means.

* * * * *